United States Patent [19]
Nakanishi

[11] Patent Number: 5,423,678
[45] Date of Patent: Jun. 13, 1995

[54] HANDPIECE HAVING BEARING PROTECTIVE MEMBER

[75] Inventor: Takasuke Nakanishi, Kanuma, Japan

[73] Assignee: Nakanishi Dental Mfg. Co., Ltd., Tochigi, Japan

[21] Appl. No.: 245,086

[22] Filed: May 17, 1994

[30] Foreign Application Priority Data

May 20, 1993 [JP] Japan .................. 5-118712

[51] Int. Cl.⁶ .................. A61C 1/05; F03B 13/04
[52] U.S. Cl. .................. 433/115; 433/132; 415/904
[58] Field of Search .............. 433/114, 115, 116, 120, 433/132; 415/904; 416/174

[56] References Cited

U.S. PATENT DOCUMENTS

| | | | |
|---|---|---|---|
| 3,132,426 | 5/1964 | White | 433/132 |
| 3,451,134 | 6/1969 | Erikson et al. | 433/115 X |
| 4,021,919 | 5/1977 | Lingenhole et al. | 433/132 |
| 4,219,330 | 8/1980 | Jaremus | 433/132 X |
| 5,074,788 | 12/1991 | Nakanishi | 433/115 |
| 5,252,065 | 10/1993 | Nakanishi | 433/115 X |

FOREIGN PATENT DOCUMENTS

296471 4/1954 Switzerland .................. 433/115

*Primary Examiner*—Nicholas D. Ucchesi
*Attorney, Agent, or Firm*—Malcolm B. Wittenberg

[57] ABSTRACT

A dental handpiece contains a sleeve for rotatably accommodating and securing a dental treatment tool therein, bearings for rotatably holding the sleeve with respect to stationary handpiece casing members, a rotatable rotor fixed to the sleeve for rotating the sleeve under action of a compressed fluid, and stationary convexed and concave protective members for sheathing the bearings exposed to an annular spacing defined by the bearings and the rotatable rotor. The rotatable rotor contains rotatable concave and convexed disc portions. The rotatable concave and convexed disc portions are arranged in proximity to the stationary convexed and concave protective members in a mating relation therewith for defining therebetween at least a first gap and a second gap communicating with the first gap and disposed radially outwardly of the first gap.

4 Claims, 3 Drawing Sheets

HANDPIECE HAVING BEARING PROTECTIVE MEMBER

BACKGROUND OF THE INVENTION

This invention relates to a dental handpiece and, more particularly, to a dental handpiece having a bearing protective member capable of preventing bearing oil shortage and terminating the suction of tooth debris into the inside of the bearing.

Up to now, a dental handpiece having a dental tool mounted thereon has been used extensively for tooth treatment. The conventional dental handpiece of the angle type is shown as an example in FIG. 5.

An angle type dental handpiece 50 has its foremost part constituted by a head housing 51 for loading a dental treatment tool 9 therein and a head housing jacket 52 connected to the head housing 51.

Within the head housing 51 at the foremost part of the dental handpiece is removably mounted a casing 57 made up of a cartridge casing 57a and a casing lid 57b. Within the casing 57 are arranged a bur sleeve 53 for receiving the dental treatment tool 9 via a reception opening 53a for securing the tool in position, a rotor 54 for rotationally driving the bur sleeve 53, an upper bearing 55 and a lower bearing 55' for rotatably supporting the bur sleeve 53 with respect to the head housing 51. A head cap 56 is threadedly mounted on the top of the head housing 51. Within the head cap 56 is mounted a chuck device, not shown, for removably holding the dental treatment tool 9 on thrusting or releasing a pushbutton 56a. Within the head housing jacket 52, there are an air supply passage 52a for supplying compressed air to the rotor 54 and an air discharge passage 52b for discharging the compressed air supplied into the inside of the head housing 51.

Radially outwardly of the bur sleeve 53 is mounted the rotor 54 in a spacing 58 between the upper bearing 55 and the lower bearing 55'. The rotor 54 acts as an air turbine rotated with the bur sleeve 53 by the compressed air supplied from the air supply passage 52a.

The above-described dental handpiece 50 has, however, a drawback that compressed air supplied via the air supply passage 52a for rotationally driving the rotor 54 is discharged to the outside of the head housing 51 via small gaps around the bearings 55, 55' exposed to the spacing 58, so that oil shortage tends to be produced in the regions of balls 55a, 55a' and retainers 55b, 55b'. Thus, it becomes necessary to replenish oil such as by oil spraying for lubricating or washing the bearings 55, 55' suffering from oil shortage. Although grease may be used in order to combat the problem of oil shortage, inconvenience may be produced such that the grease tends to flow out of the head housing 51.

There is also a problem that, during the standstill of the rotation of the air turbine, negative pressure tends to be produced within the inside of the head housing 51 and, under the pressure difference between the inside and the outside of the head housing 51, tooth debris, saliva or blood tend to be sucked from the outside into the inside of the head housing 51 via the pap between the bur sleeve 53 on the one hand and the head housing 51 and the casing 57 on the other hand, thus producing damages to the race surfaces or abrasion of the balls 55a, 55a' or the retainers 55b, 55b' of the bearings 55, 55'.

SUMMARY OF THE INVENTION

In view of the above problems of the prior art, it is a principal object of the present invention to provide a dental handpiece in which oil shortage may be prevented from being produced at the bearing balls and retainers and in which there is no risk of tooth debris, saliva, blood or the like being sucked into the inside of the head housing.

The above and other objects of the present invention will become apparent from the following description.

According to the present invention, there is provided a dental handpiece comprising sleeve means for rotatably accommodating and securing a dental treatment tool therein, bearing means for rotatably holding the sleeve means with respect to stationary handpiece casing members, rotatable rotor means fixed to the sleeve means for rotating the sleeve means under the action of a compressed fluid, and stationary convexed and concave protective members for sheathing the bearing means exposed to an annular spacing defined by the bearing means and the rotatable rotor means, the rotatable rotor means comprising rotatable concave and convexed disc portions, the rotatable concave and convexed disc portions being arranged in proximity to the stationary convexed and concave protective members in a mating relation therewith for defining at least a first gap and a second gap communicating with the first gap and disposed radially outwardly of the first gap.

PREFERRED EMBODIMENTS OF THE INVENTION

Figure 1:
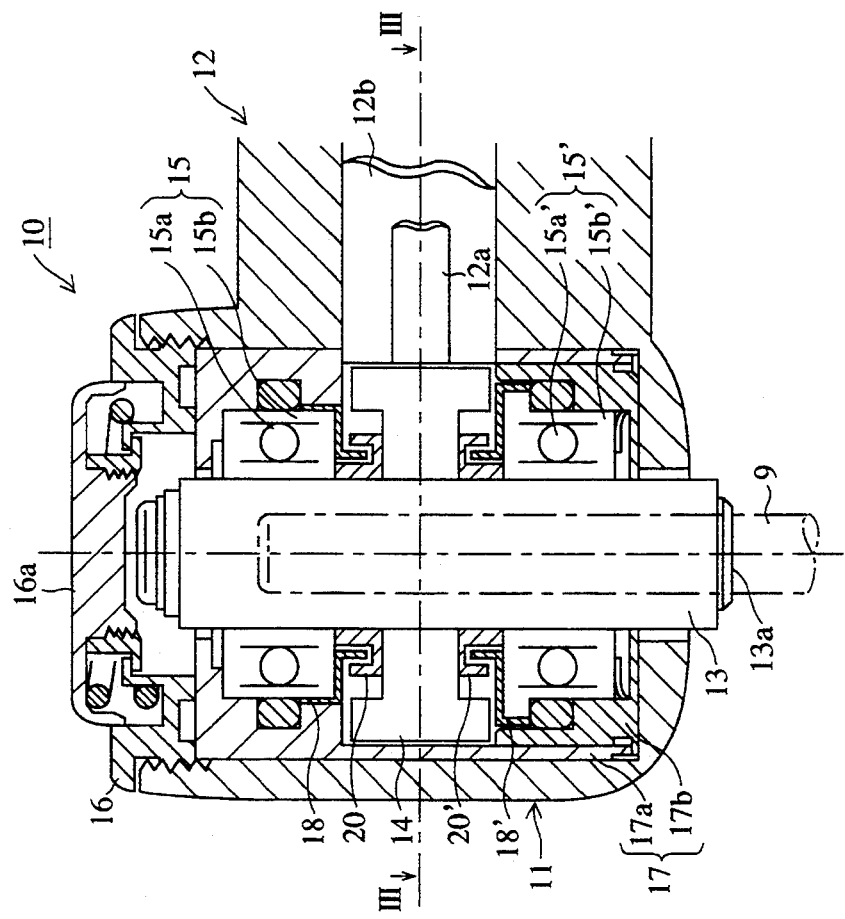
FIG. 1 is a longitudinal cross-sectional view showing the foremost part of a dental handpiece according to the present invention.

Referring to FIG. 1, a dental handpiece 10 of the present invention has its foremost part constituted by a head housing 11 for loading a dental treatment tool 9 thereon and a head housing jacket 12 connected to the head housing 11.

Within the head housing 11 at the foremost part of the handpiece 10 is removably contained a casing 17 comprised of a cartridge casing 17a and a casing lid 17b. Within the casing 17, there are arranged a bur sleeve 13 for receiving the dental treatment tool 9 via a reception opening 13a for securing the tool in position, a rotor 14 for rotationally driving the bur sleeve 13, an upper bearing 15 and a lower bearing 15' for rotatably supporting the bur sleeve 13 with respect to the head housing 11.

A head cap 16 is threadedly mounted on the top of the head housing 11. Within the head cap 16, there is mounted a chuck device, not shown, for removably holding the dental treatment tool 9 on thrusting or releasing a pushbutton 16a. Within the head housing jacket 12 are arranged an air supply passage 12a for supplying compressed air to the rotor 14 and an air discharge passage 12b for discharging the compressed air supplied into the inside of the head housing jacket 12 and used for rotating the rotor 14.

Radially outwardly of the bur sleeve 13 are arranged the upper bearing 15 and the lower bearing 15' made up of balls 15a, 15a' and retainers 15b, 15b', respectively, and the rotor 14 is arranged within a spacing 23 (see FIG. 2) defined between the upper bearing 15 and the lower bearing 15'. The rotor 14 acts as an air turbine rotated with the bur sleeve 13 by the compressed air supplied from an air supply passage 12a (FIG. 3).

Figure 2:
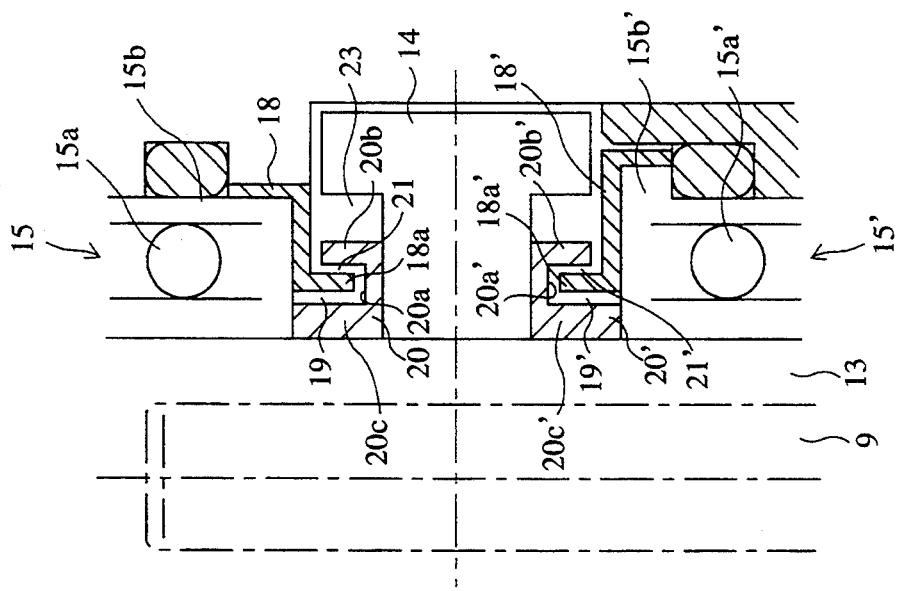
FIG. 2 is an enlarged partial cross-sectional view showing a rotor part of the dental handpiece shown in FIG. 1.
Figure 3:
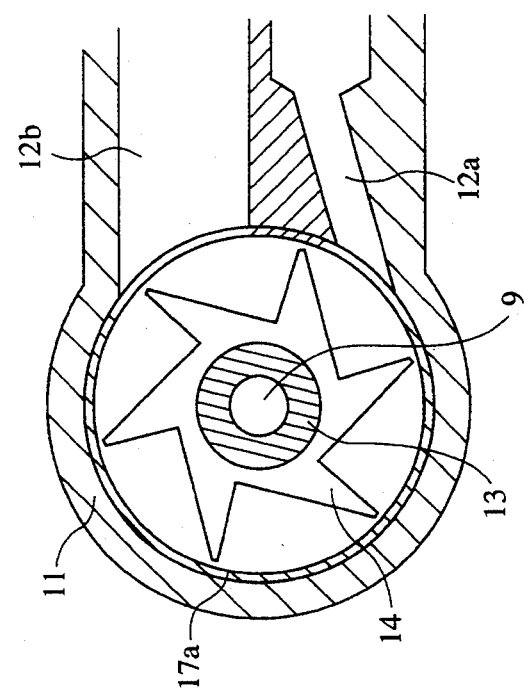
FIG. 3 is a lateral cross-sectional view taken along line III—III of FIG. 1.
Figure 5:
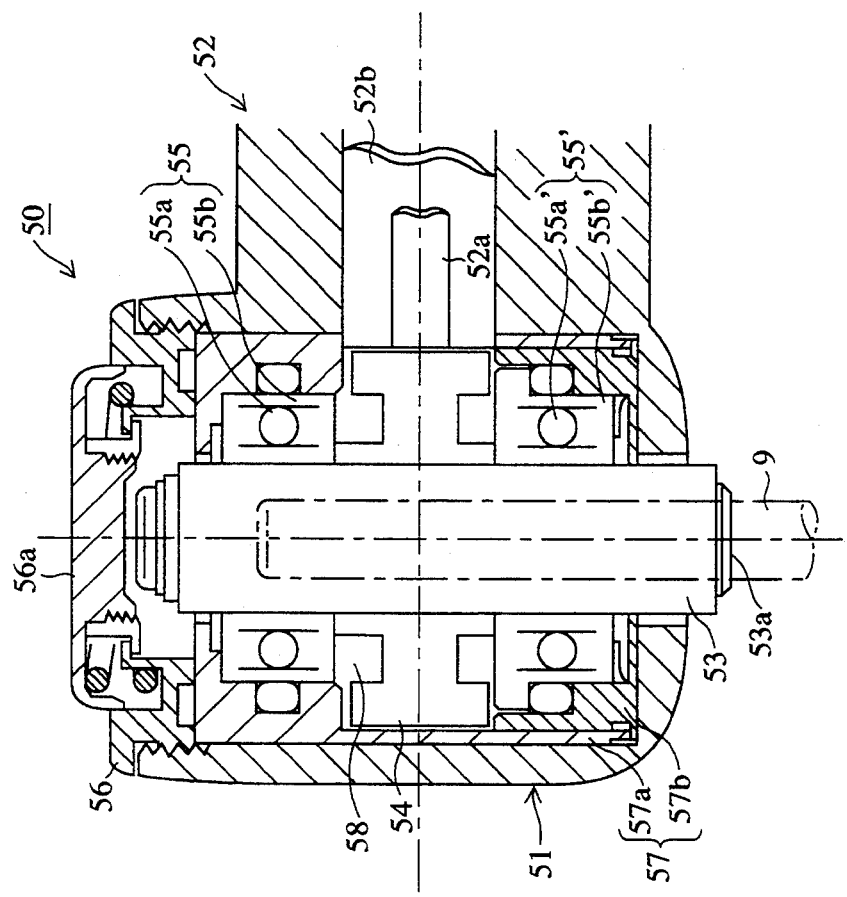
FIG. 5 is an enlarged longitudinal cross-sectional view showing the foremost part of a conventional dental handpiece.

As shown in detail and on an enlarged scale in FIG. 2, stationary discs 18, 18' are secured on the bottom of the retainer 15b of the bearing 15 and on the top of the retainer 15b' of the bearing 15'. On the top and on the bottom of the rotor 14 are secured rotary discs 20, 20' rotated with the rotor 14.

The stationary discs 18, 18' include annular protrusions 18a, 18a' protruding in the direction of the rotor 14, while the rotary discs 20, 20' include annular recesses 20a, 20a' in proximity to the annular protrusions 18a, 18a' for accommodating these protrusions. Annular first gaps 19, 19' and second gaps 21, 21' radially outwardly spaced apart from and communicating with the first gaps 19, 19' are defined between the protrusions 18a, 18a' and the recesses 20a, 20a'.

When the rotor 14 and the bur sleeve 13 are rotated by compressed air for cutting teeth and the like, the rotary discs 20, 20' are also rotated in unison with the rotor 14 and the bur sleeve 13. The radially outwardly situated annular protrusions 20b, 20b' of the rotary discs 20, 20' are rotated at a peripheral velocity faster than radially central portions 20c, 20c'. Since the second gaps 21, 21' are situated radially outwardly of the first gaps 19, 19' the air flow velocity accompanied by the rotation of the rotor 14 is faster at the second gaps 21, 21' than at the first gaps 19, 19', such that the second gaps 21, 21' are at lower pressures than the first gaps 19, 19'. Consequently, the compressed air supplied via the air supply passage 12a may be prevented from being discharged out of the head housing 11 from the second gaps 21, 21' via the first gaps 19, 19' and the bearings 15, 15', thereby preventing the oil shortage of the bearings 15, 15'.

On the other hand, the stationary discs 18, 18' and the rotary discs 20, 20' sheathe the bearings 15, 15', respectively, for interrupting air communication with the outside. Consequently, even when negative pressure is produced in the inner spacing 23 on interrupting the rotation of the rotor 14, the tooth debris or the like may be prevented from being sucked via the gap between the bur sleeve 13 and the head housing 11 and through the bearings 15, 15'.

Figure 4:
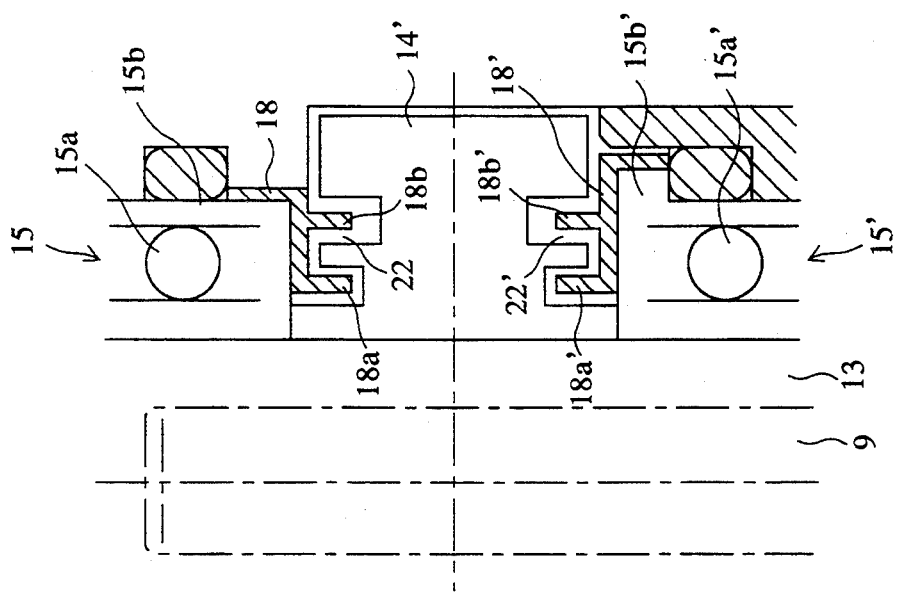
FIG. 4 is an enlarged partial cross-sectional view showing a rotor of a dental handpiece according to another embodiment of the present invention.

Although the rotary discs 20, 20' in the above-described embodiment are secured to the rotor 14 rotated in unison with the bur sleeve 13, the present invention is not limited thereto and may also be applied to an integral type rotor 14' in which the rotor 14 is mounted integrally with the rotary discs 20, 20', as shown in FIG. 4. The stationary discs 18, 18' may also be additionally provided with annular protrusions 18b, 18b', respectively. In such case, third gaps 22, 22' are further produced in which the air flow velocity is the fastest and the air pressure becomes the smallest.

Although the present embodiments are directed to the angle type dental handpiece, the present invention may also be applied to a straight type dental handpiece.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A dental handpiece comprising: sleeve means for rotatably accommodating and securing a dental treatment tool therein, stationary handpiece casing members disposed outside of said sleeve member, rotatable rotor means fixed to said sleeve means for rotating said sleeve means under action of a compressed fluid, upper and lower bearing means for rotatably holding the sleeve means with respect to said stationary handpiece casing members, annular spacings defined between said upper bearing means and said rotatable rotor means and between said lower bearing means and said rotatable rotor means, respectively, stationary upper and lower protective members each having an annular protrusion protruding into a respective one of said annular spacings and sheathing said upper and lower bearing means, said rotatable rotor means comprising further upper and lower rotatable disc portions each having an annular recess which receives a respective one of said annular protrusions, said rotatable disc portions being arranged in proximity to said stationary protective members in a mating relation therewith and defining therebetween at least a first annular gap and a second annular gap communicating with said first gap and disposed radially outwardly of said first gap.

2. The dental handpiece as claimed in claim 1 wherein said rotor means comprises a main rotor body and said rotatable disc portions are secured to said main rotor body.

3. The dental handpiece as claimed in claim 1 wherein said rotor means comprises a main rotor body wherein said rotatable disc portions are integrally formed thereon.

4. The dental handpiece as claimed in claim 1 wherein a third gap in communication with and disposed radially outwardly of said second gap is further defined between each of said stationary protective members and said rotatable disc portions of the rotatable means.

* * * * *